US011445889B2

(12) United States Patent
Ueda

(10) Patent No.: US 11,445,889 B2
(45) Date of Patent: Sep. 20, 2022

(54) ENDOSCOPE AID AND ENDOSCOPE

(71) Applicant: FUJIFILM Corporation, Tokyo (JP)

(72) Inventor: Yoshihiro Ueda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 542 days.

(21) Appl. No.: 16/516,265

(22) Filed: Jul. 19, 2019

(65) Prior Publication Data

US 2020/0046205 A1 Feb. 13, 2020

(30) Foreign Application Priority Data

Aug. 7, 2018 (JP) .............................. JP2018-148831

(51) Int. Cl.
*A61B 1/00* (2006.01)
*A61B 1/005* (2006.01)
*A61B 1/012* (2006.01)
*A61B 1/018* (2006.01)
(Continued)

(52) U.S. Cl.
CPC ........ *A61B 1/00087* (2013.01); *A61B 1/0051* (2013.01); *A61B 1/00101* (2013.01); *A61B 1/00119* (2013.01); *A61B 1/00131* (2013.01); *A61B 1/0125* (2013.01); *A61B 1/051* (2013.01); *A61B 1/00094* (2013.01); *A61B 1/00165* (2013.01); *A61B 1/018* (2013.01); *A61B 1/0661* (2013.01)

(58) Field of Classification Search
CPC ............ A61B 1/00087; A61B 1/00094; A61B 1/00119; A61B 1/018
See application file for complete search history.

(56) References Cited

U.S. PATENT DOCUMENTS 10,881,277 B2 1/2021 Hassidov et al.
2008/0287961 A1 11/2008 Miyamoto et al.
(Continued)

FOREIGN PATENT DOCUMENTS

| EP | 1955643 | 8/2008 |
| JP | H09154805 | 6/1997 |
| JP | 2009118891 | 6/2009 |

(Continued)

OTHER PUBLICATIONS

"Search Report of Europe Counterpart Application", dated Dec. 13, 2019, p. 1-p. 9.
(Continued)

*Primary Examiner* — Matthew J Kasztejna
(74) *Attorney, Agent, or Firm* — JCIPRNET

(57) ABSTRACT

An endoscope aid attachably and detachably attached to a treatment tool insertion channel of an endoscope includes a flexible tubular-member longer than a total length of the treatment tool insertion channel. The tubular-member has a treatment tool insertion pipe line and a suction pipe line. A distal end part of the tubular-member has a sliding contact part that has an outer periphery coming in sliding contact with an inner peripheral surface of an outlet portion of the treatment tool insertion channel maintained in the shape of a straight pipe irrespective of bending of a bending part of the endoscope and is disposed in the outlet portion, and an extending part that extends from the sliding contact part to a distal end side and is disposed to protrude from an outlet of the treatment tool insertion channel. A distal-end-side opening of the suction pipe line is provided in the extending part.

14 Claims, 14 Drawing Sheets

(51) Int. Cl.
   *A61B 1/05*   (2006.01)
   *A61B 1/06*   (2006.01)

(56) References Cited

U.S. PATENT DOCUMENTS

2014/0358088 A1   12/2014   Miyamoto et al.
2021/0076906 A1   3/2021    Hassidov et al.

FOREIGN PATENT DOCUMENTS

| | | |
|---|---|---|
| JP | 2011251140 | 12/2011 |
| JP | 2018519016 | 7/2018 |
| KR | 101819574 | 1/2018 |
| WO | 2007063904 | 6/2007 |

OTHER PUBLICATIONS

"Office Action of Japan Counterpart Application" with English translation thereof, dated Sep. 7, 2021, p. 1-p. 7.
Office Action of European Counterpart Application, dated Mar. 10, 2021, pp. 1-7.
"Office Action of Japan Counterpart Application" with English translation thereof, dated Mar. 8, 2022, p. 1-p. 5.

ENDOSCOPE AID AND ENDOSCOPE

CROSS-REFERENCE TO RELATED APPLICATIONS

The present application claims priority under 35 U.S.C. § 119 to Japanese Patent Application No. 2018-148831, filed on Aug. 7, 2018. Each of the above application(s) is hereby expressly incorporated by reference, in its entirety, into the present application.

BACKGROUND OF THE INVENTION

1. Field of the Invention

The present invention relates to an endoscope aid and an endoscope.

2. Description of the Related Art

A guide catheter described in WO2007/063904A is inserted into an insertion part from a channel opening part provided in an operating part of an endoscope, and a distal end portion of the guide catheter is delivered from a distal end part of the insertion part. The guide catheter comprises a guide catheter insertion part and a guide part extending from a distal end surface of the guide catheter insertion part. The guide catheter has a treatment tool channel through which a treatment tool is insertable through, and a plurality of fluid supply channels used for injection of a contrast medium, water supply, suction, and the like, the treatment tool channel opens to the distal end surface of the guide catheter insertion part, and the fluid supply channel opens to a distal end surface of the guide part.

SUMMARY OF THE INVENTION

The internal diameters of treatment tool insertion channels of endoscopes are variously different. For example, the internal diameter of a treatment tool insertion channel of an oral endoscope is larger than the internal diameter of a treatment tool insertion channel of a transnasal endoscope. The sizes of treatment tools are variously different. For example, there is a case where a treatment tool with a relatively small size is preferably used for the treatment that requires an accurate treatment tool operation. Here, in a case where the internal diameter of a treatment tool insertion channel is excessive with respect to the size of a treatment tool, the disposition of the treatment tool is not settled in an outlet portion of the treatment tool insertion channel, and the difficulty of treatment increases unnecessarily. On the other hand, changing endoscopes in accordance with treatment imposes a burden on a subject. Hence, in one endoscope, the internal diameter of a treatment tool insertion channel is desired to be changed depending on situations.

Additionally, generally, a suction tube of an endoscope joins a treatment tool insertion channel, and the treatment tool insertion channel is also used for suction of liquid, such as blood. In a case where a treatment target part bleeds in a case where treatment is performed, the blood is suctioned, and hemostasis is performed. However, a field of view narrows by bringing an outlet of the treatment tool insertion channel serving as a suction port close to a bleeding spot.

The guide catheter described in WO2007/063904A has the treatment tool channel through which a treatment tool is insertable, and the internal diameter of the treatment tool insertion channel of the endoscope is changed as the guide catheter is inserted into the treatment tool insertion channel of the endoscope. Moreover, the guide catheter has a fluid supply channel to be used for suction or the like, and the guide part provided with an opening of the fluid supply channel is disposed to protrude from the outlet of the treatment tool insertion channel of the endoscope. For this reason, it is possible to maintain the field of view even at the time of suction using the fluid supply channel. However, the disposition of the guide catheter in the outlet portion of the treatment tool insertion channel of the endoscope is not taken into consideration at all. In the outlet portion of the treatment tool insertion channel of the endoscope, in a case where the disposition of the guide catheter is not stable, the disposition of the treatment tool inserted through the treatment tool channel of the guide catheter is also not stable.

The invention has been made in view of the above-described circumstances, and an object thereof is to provide an endoscope aid that is capable of changing the internal diameter of a treatment tool insertion channel of an endoscope in accordance with situations, can stabilize the disposition of a treatment tool in an outlet portion of the treatment tool insertion channel, and can also perform suction is provided, and an endoscope comprising a treatment tool insertion channel to which the endoscope aid is attachable.

An endoscope aid of an aspect of the invention is an endoscope aid attachably and detachably attached to a treatment tool insertion channel of an endoscope. The endoscope aid comprises a flexible tubular member longer than a total length of the treatment tool insertion channel. The tubular member has a treatment tool insertion pipe line that extends from a proximal end part of the tubular member disposed on an inlet side of the treatment tool insertion channel to a distal end part of the tubular member, and a suction pipe line that is provided separately from the treatment tool insertion pipe line. The distal end part of the tubular member has a sliding contact part that has an outer periphery coming in sliding contact with an inner peripheral surface of an outlet portion of the treatment tool insertion channel maintained in the shape of a straight pipe irrespective of bending of an endoscope bending part and is disposed in the outlet portion, and an extending part that extends from the sliding contact part to a distal end side and is disposed to protrude from an outlet of the treatment tool insertion channel. A distal-end-side opening of the suction pipe line is provided in the extending part.

Additionally, an endoscope of an aspect of the invention comprises a treatment tool insertion channel to which the above endoscope aid is attachable.

According to the invention, it is possible to the endoscope aid that is capable of changing the internal diameter of the treatment tool insertion channel of the endoscope in accordance with situations, can stabilize the disposition of the treatment tool in the outlet portion of the treatment tool insertion channel, and can also perform suction, and it is possible to provide the endoscope comprising treatment tool insertion channel to which the endoscope aid is attachable.

DESCRIPTION OF THE PREFERRED EMBODIMENTS

Figure 1:
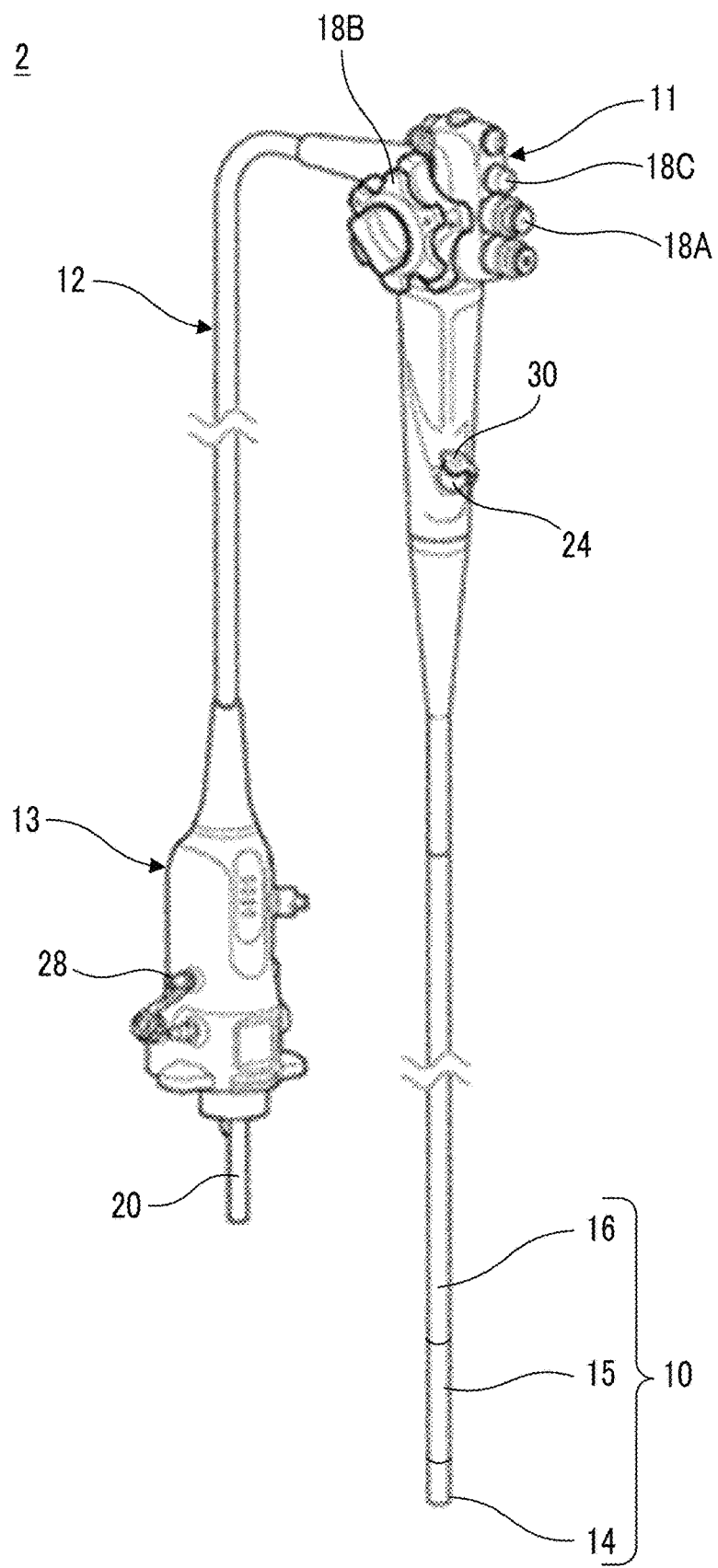
FIG. 1 is a perspective view of an example of an endoscope for describing an embodiment of the invention.
Figure 2:
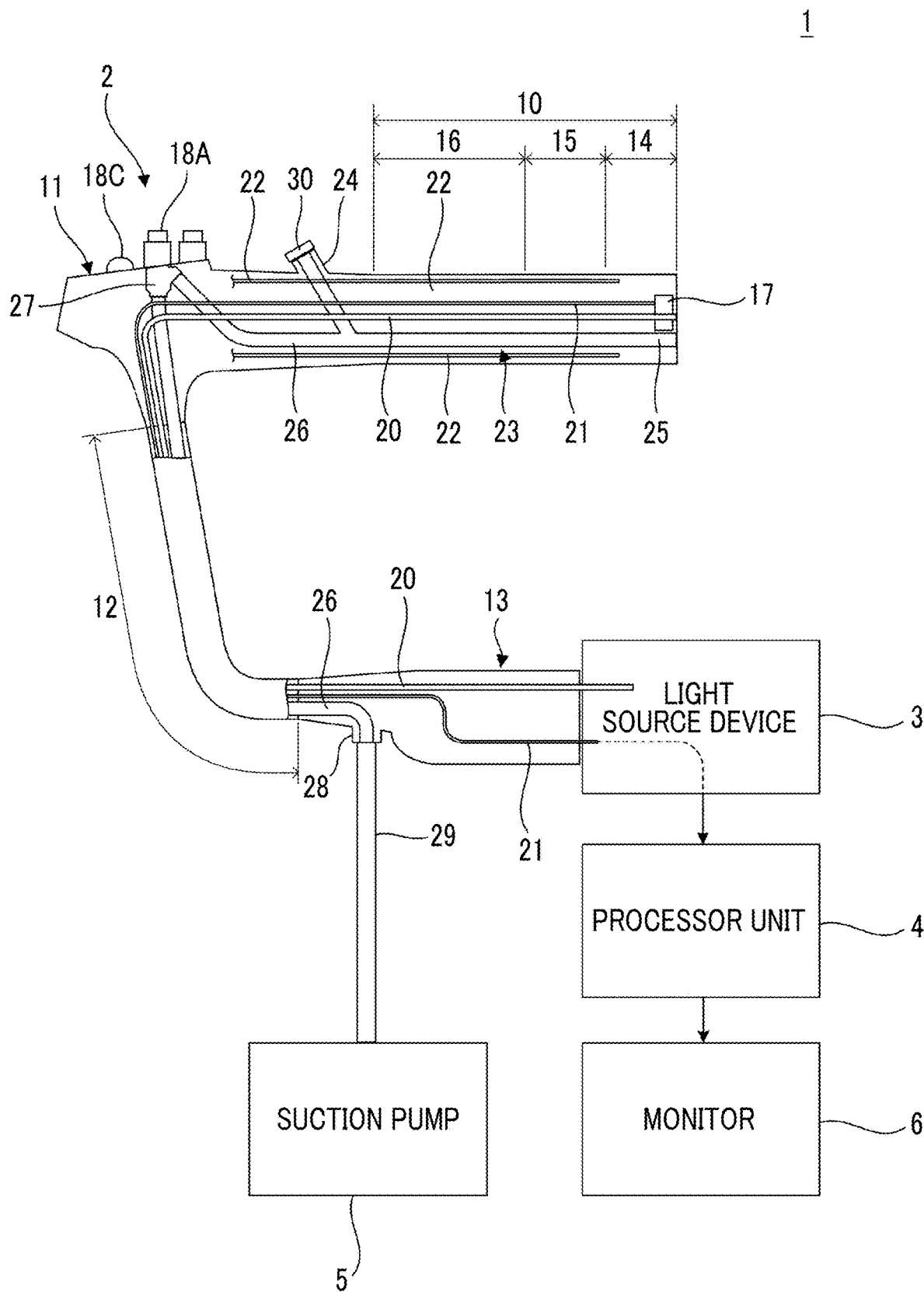
FIG. 2 is a schematic view of an example of an endoscope system including the endoscope of FIG. 1.

FIG. 1 illustrates an example of an endoscope for describing an embodiment of the invention, and FIG. 2 illustrates an example of an endoscope system including the endoscope of FIG. 1.

The endoscope system 1 comprises an endoscope 2, a light source device 3, a processor unit 4, and a suction pump 5. An endoscope 2 has an insertion part 10 to be inserted into a subject, an operating part 11 connected to the insertion part 10, and a universal cord 12 extending from the operating part 11, and a terminal of the universal cord 12 is provided with a connector 13 to be connected to the light source device 3.

The insertion part 10 is constituted of a distal end part 14, a bending part 15 connected to the distal end part 14, and a flexible part 16 that connects the bending part 15 and the operating part 11 to each other. An imaging unit 17 including imaging elements, such as a charge coupled device (CCD) image sensor and a complementary metal oxide semiconductor (CMOS) image sensor, is mounted on the distal end part 14. The bending part 15 is configured to be bendable, and bending of the bending part 15 is operated by the operating part 11. Additionally, the flexible part 16 is configured to be flexible so as to be deformable along the shape of an insertion path of the subject.

The operating part 11 is provided with an operation button 18A that operates suction using the suction pump 5, an operation knob 18B that operates the bending of the bending part 15, an operation button 18C that operates imaging using the imaging unit 17, and the like. Additionally, the operating part 11 is provided with an inlet portion 24 of the treatment tool insertion channel 23 through which a treatment tool is inserted.

A light guide 20 and an electrical cable 21 are provided inside the insertion part 10, the operating part 11, and the universal cord 12. The light guide 20 guides illumination light, that is to be generated by the light source device 3, to the distal end part 14. The electrical cable 21 transmits operating power, control signals, and captured image signals of the imaging unit 17 between the imaging unit 17 and the processor unit 4. The processor unit 4 generates captured image data from input captured image signals, and causes the generated captured image data to be displayed on the monitor 6 and recorded.

A plurality of operating wires 22 and a treatment tool insertion channel 23 are provided inside the insertion part 10 and the operating part 11. The operating wires 22 reach the distal end part 14 of the insertion part 10 from the operating part 11, and are pushed toward the distal end part 14 or pulled toward the operating part 11 in accordance with the operation of the operation knob 18B of the operating part 11. The bending part 15 of the insertion part 10 is bent in accordance with the push/pull of the operating wire 22. The treatment tool insertion channel 23 reaches the distal end part 14 of the insertion part 10 from the inlet portion 24 provided in the operating part 11, and an outlet portion 25 of the treatment tool insertion channel 23 opens to a distal end surface of the distal end part 14. A treatment tool inserted into the treatment tool insertion channel 23 through the opening of the inlet portion 24 is guided to the distal end part 14 of the insertion part 10 by the treatment tool insertion channel 23, and protrudes from the distal end part 14 through the opening of the outlet portion 25.

The treatment tool insertion channel 23 joins a suction tube 26 in the operating part 11. The suction tube 26 extends to the connector 13 via a valve 27 opened and closed by the operation button 18A, and is connected to the suction pump 5 via the connection tube 29 connected to a mouthpiece 28 provided in the connector 13. By opening the valve 27, liquid, such as blood, is suctioned from the opening of the outlet portion 25 of the treatment tool insertion channel 23 through the suction tube 26 to the suction pump 5. In addition, a forceps valve 30 having an on-off valve is mounted on the inlet portion 24, and as the opening of the inlet portion 24 is closed by the forceps valve 30 at the time of suction, the internal pressure of the treatment tool insertion channel 23 is negative.

Figure 3:
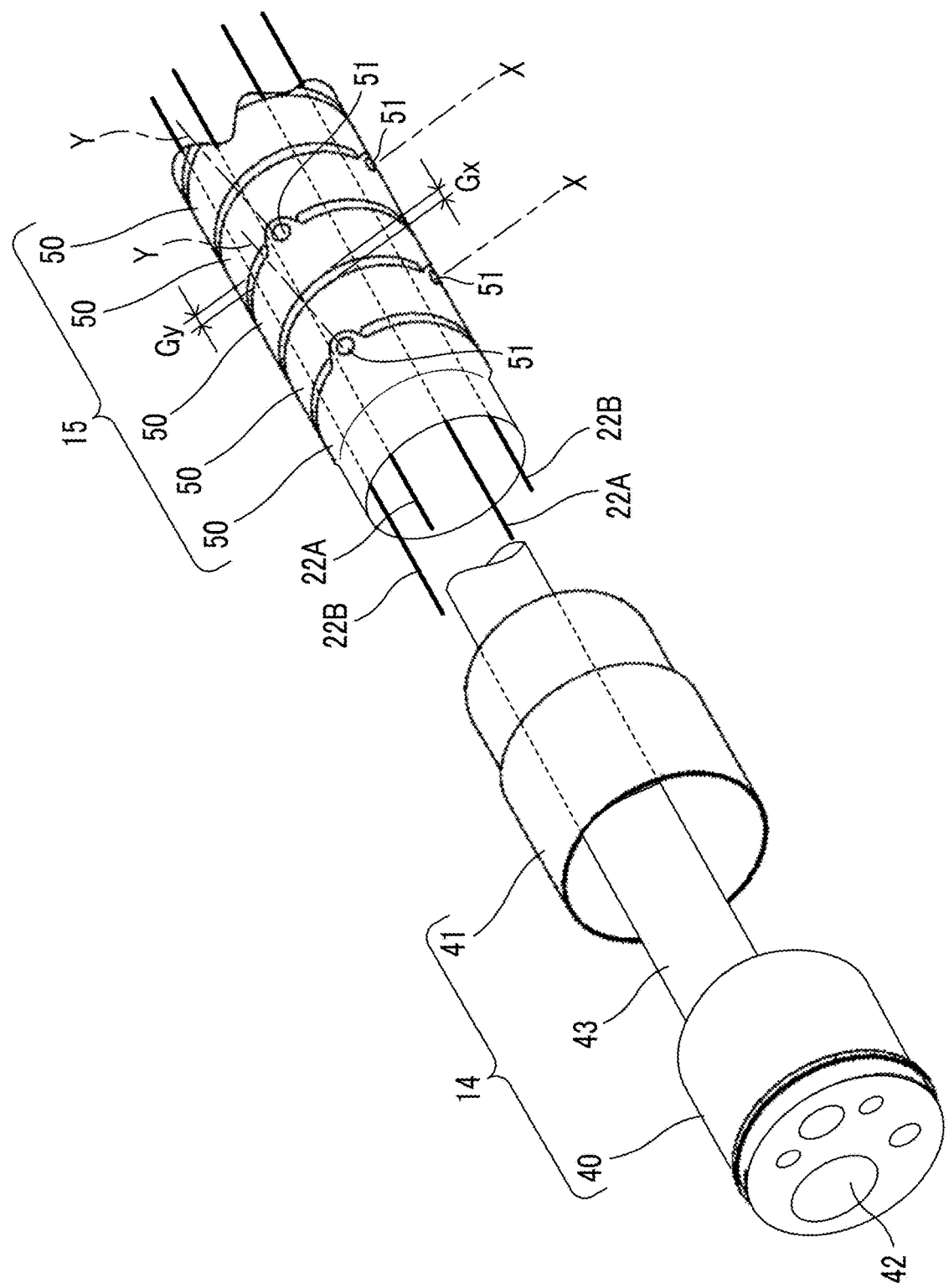
FIG. 3 is a perspective view illustrating an internal mechanism of a distal end part and a bending part of an insertion part of the endoscope of FIG. 1.

FIG. 3 illustrates an internal mechanism of the distal end part 14 and the bending part 15 of the insertion part 10.

The distal end part 14 has a columnar distal end rigid part 40 that holds various built-in elements, such as the imaging unit 17 (refer to FIG. 2) and the like, to be mounted on the distal end part 14, and a cylindrical distal end sleeve 41 to be fixed to a proximal end side of the distal end rigid part 40. A through-hole 42, which passes through the distal end rigid part 40 in an axial direction and has a circular cross-sectional shape, is formed in the distal end rigid part 40. A flexible channel tube 43, which constitutes the treatment tool insertion channel 23 and has a circular cross-sectional shape, is joined to the distal end rigid part 40. An inner hole of the channel tube 43 joined to the distal end rigid part 40, and the through-hole 42 communicate with each other, and the through-hole 42 constitutes at least a portion of the outlet portion 25 of the treatment tool insertion channel 23.

The bending part 15 has a plurality of annular pieces 50, and the pieces 50 are arranged with their central axes aligned with each other. A piece 50 disposed nearest to the distal end part 14 side among the plurality of pieces 50 is fixed to the distal end sleeve 41 of the distal end part 14. Two adjacent pieces 50 are coupled to each other so as to be rotationally movable by a pair of shaft members 51 disposed on an axis orthogonal to a longitudinal axis of the bending part 15. As the rotational movements of the two adjacent pieces 50 are combined together, the bending part 15 is bent as a whole.

In the example illustrated in FIG. 3, a rotational movement axis X and a rotational movement axis Y substantially perpendicular to the rotational movement axis X are alternately provided as rotational movement axes of the two adjacent pieces 50. The bending part 15 is capable of being bent in a total of four directions of upward-downward directions based on the rotational movement around the rotational movement axes X of the two adjacent pieces 50 and leftward-rightward directions based on the rotation movement around the rotational movement axes Y of the two adjacent pieces 50.

In addition, the maximum bending angle of the bending part 15 in the upward-downward directions and the maximum bending angle of the bending part 15 in the leftward-rightward directions may be the same as or different from each other. For example, the maximum bending angles in the upward-downward directions can be made relatively large by making the number of sets of two pieces 50 rotationally movable around the rotational movement axis X more than the number of sets of two rotationally movable pieces 50 rotationally movable around the rotational movement axis Y.

Additionally, the maximum rotational movement angles of respective sets of two pieces 50 rotationally movable around the rotational movement axis X may be the same as or different from each other, and the maximum rotational movement angle of each set can be set depending on a spacing Gx between the two pieces 50. Similarly, the maximum rotational movement angles of respective sets of two pieces 50 rotationally movable around the rotational movement axis Y may be the same as or different from each other, and the maximum rotational movement angle of each set can be set depending on a spacing Gy between the two pieces 50.

A pair of operating wires 22A corresponding to bending in the upward-downward directions, a pair of operating wires 22B corresponding to bending in the leftward-rightward directions are provided as the plurality of operating wires 22 (refer to FIG. 2). The pair of operating wires 22A and the pair of operating wires 22B reach the distal end part 14 from the operating part 11 through the insides of the plurality of pieces 50, and are fixed to the distal end sleeve 41, respectively. Additionally, the channel tube 43 that forms the treatment tool insertion channel 23 also reaches the distal end part 14 from the operating part 11 through the insides of the plurality of pieces 50, and is joined to the distal end rigid part 40.

Figure 4:
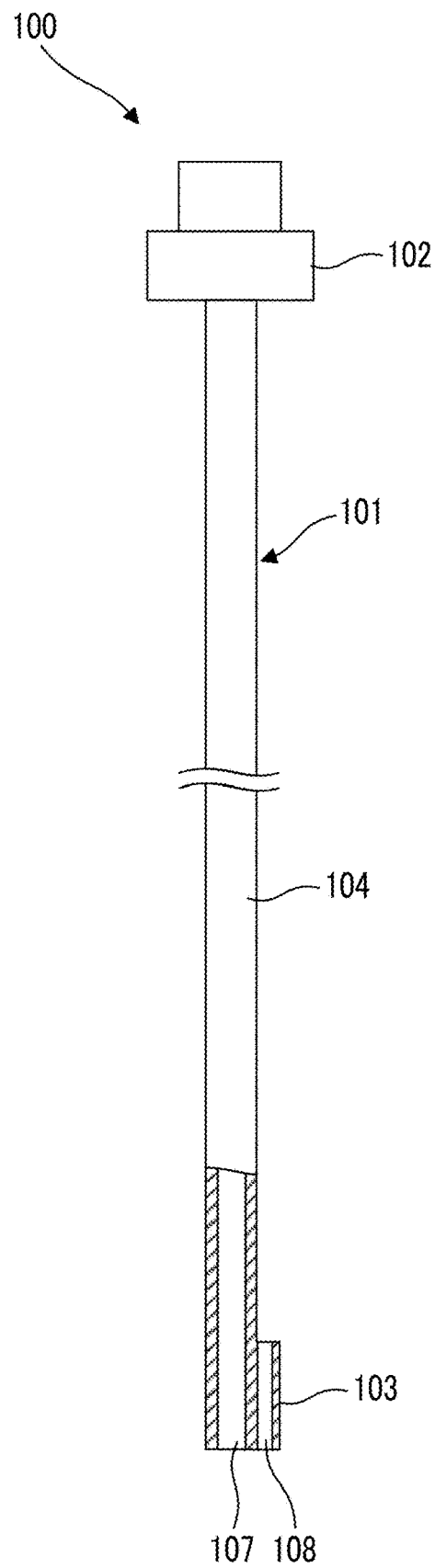
FIG. 4 is a plan view of an example of an endoscope aid for describing the embodiment of the invention.

FIG. 4 illustrates an example of the endoscope aid for describing the embodiment of the invention.

An endoscope aid 100 illustrated in FIG. 4 is attachably and detachably attached to the treatment tool insertion channel 23 of the endoscope 2. The endoscope aid 100 has a flexible tubular member 101 having a circular cross-sectional shape, and a mouthpiece 102 coupled to a proximal end part of the tubular member 101. The tubular member 101 is inserted into the treatment tool insertion channel 23 through the opening of the inlet portion 24 of the treatment tool insertion channel 23. The mouthpiece 102 is attachably and detachably mounted to the inlet portion 24.

The tubular member 101 is longer than the total length of the treatment tool insertion channel 23, and with the mouthpiece 102 being mounted on the inlet portion 24 of the treatment tool insertion channel 23, a distal end part 103 of the tubular member 101 reaches the outlet portion 25 of the treatment tool insertion channel 23, and a portion of the distal end part 103 on the distal end side protrudes from the opening (outlet) of the outlet portion 25. Additionally, the other portion excluding the distal end part 103 of the tubular member 101 is a smaller-diameter part 104 thinner than the distal end part 103.

With reference to FIGS. 5 to 8, the outlet portion 25 of the treatment tool insertion channel 23 will be described.

As described above, the channel tube 43 constituting the treatment tool insertion channel 23 reaches the distal end part 14 of the insertion part 10 through the insides of the plurality of pieces 50 included in the bending part 15 of the insertion part 10, and is joined to the distal end rigid part 40 of the distal end part 14, and the inner hole of the channel tube 43 communicates with the through-hole 42 of the distal end rigid part 40. Although the channel tube 43 is bent in accordance with the bending of the bending part 15, the outlet portion 25 of the treatment tool insertion channel 23 means a portion that is maintained in the shape of a straight pipe irrespective of the bending of the bending part 15.

Figure 5:
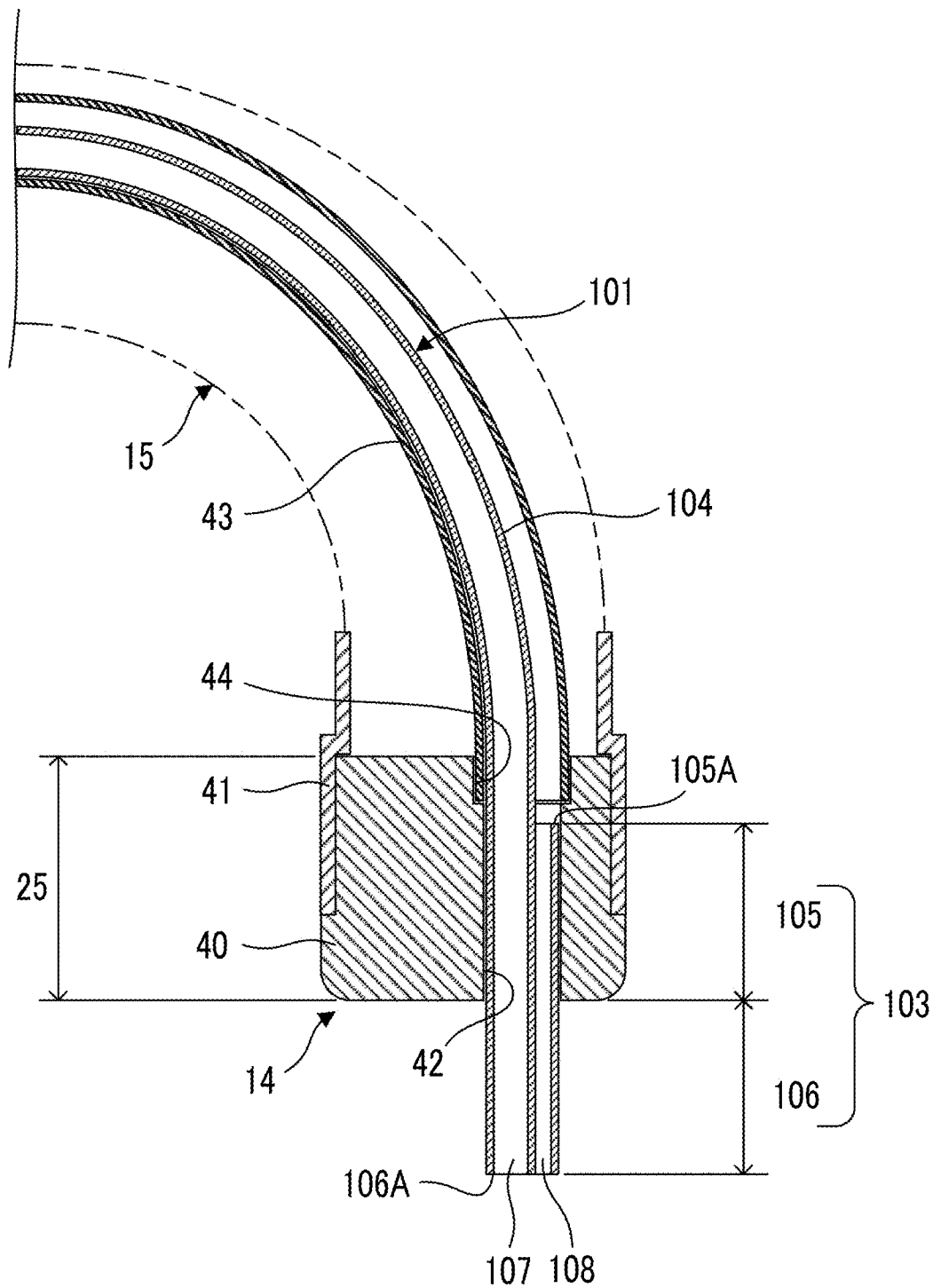
FIG. 5 is a cross-sectional view of an example of an outlet portion of a treatment tool insertion channel in a state where the endoscope aid of FIG. 4 is attached to the treatment tool insertion channel of the endoscope of FIG. 1.

In the example illustrated in FIG. 5, a fitting hole 44, which is coaxial with the through-hole 42 and has a larger diameter than the through-hole 42, is formed in a proximal end part of the distal end rigid part 40. A distal end of the channel tube 43 is internally fitted to the fitting hole 44, and is joined to the distal end rigid part 40 by bonding or the like. The through-hole 42 and the fitting hole 44 are maintained in the shape of a straight pipe irrespective of the bending of the bending part 15. In this case, the outlet portion 25 of the treatment tool insertion channel 23 is constituted of the through-hole 42 and the fitting hole 44.

Figure 6:
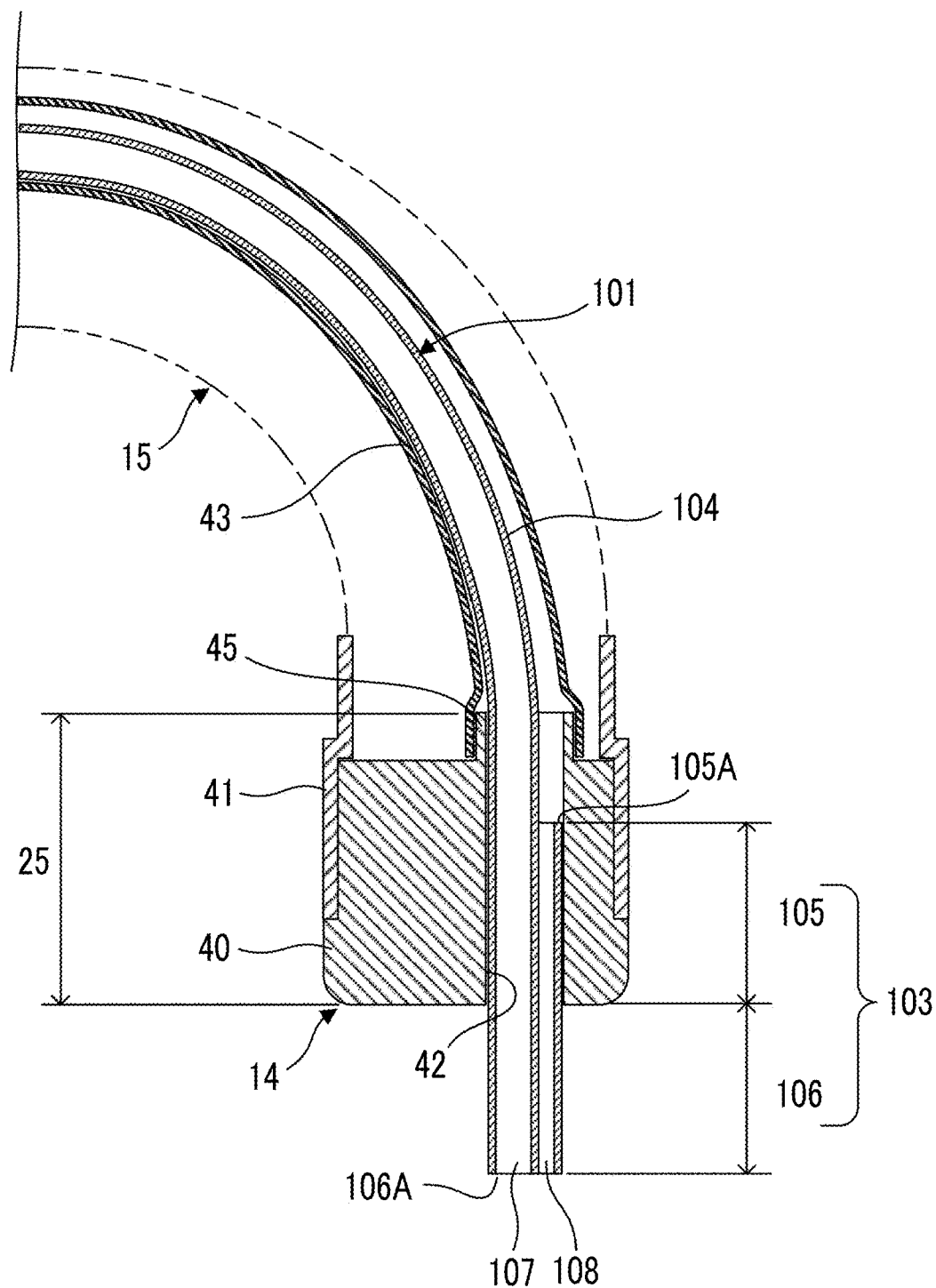
FIG. 6 is a cross-sectional view of another example of the outlet portion of the treatment tool insertion channel in the state where the endoscope aid of FIG. 4 is attached to the treatment tool insertion channel of the endoscope of FIG. 1.

In the example illustrated in FIG. 6, an annular protrusion 45, which is coaxial with the through-hole 42 and has the same internal diameter as the internal diameter of the through-hole 42, is formed in the proximal end part of the distal end rigid part 40 integrally with the distal end rigid part 40. The distal end of the channel tube 43 is externally fitted to the annular protrusion 45. The through-hole 42 and the annular protrusion 45 are maintained in the shape of a straight pipe irrespective of the bending of the bending part 15. In this case, the outlet portion 25 of the treatment tool insertion channel 23 is constituted of the through-hole 42 and the annular protrusion 45.

Figure 7:
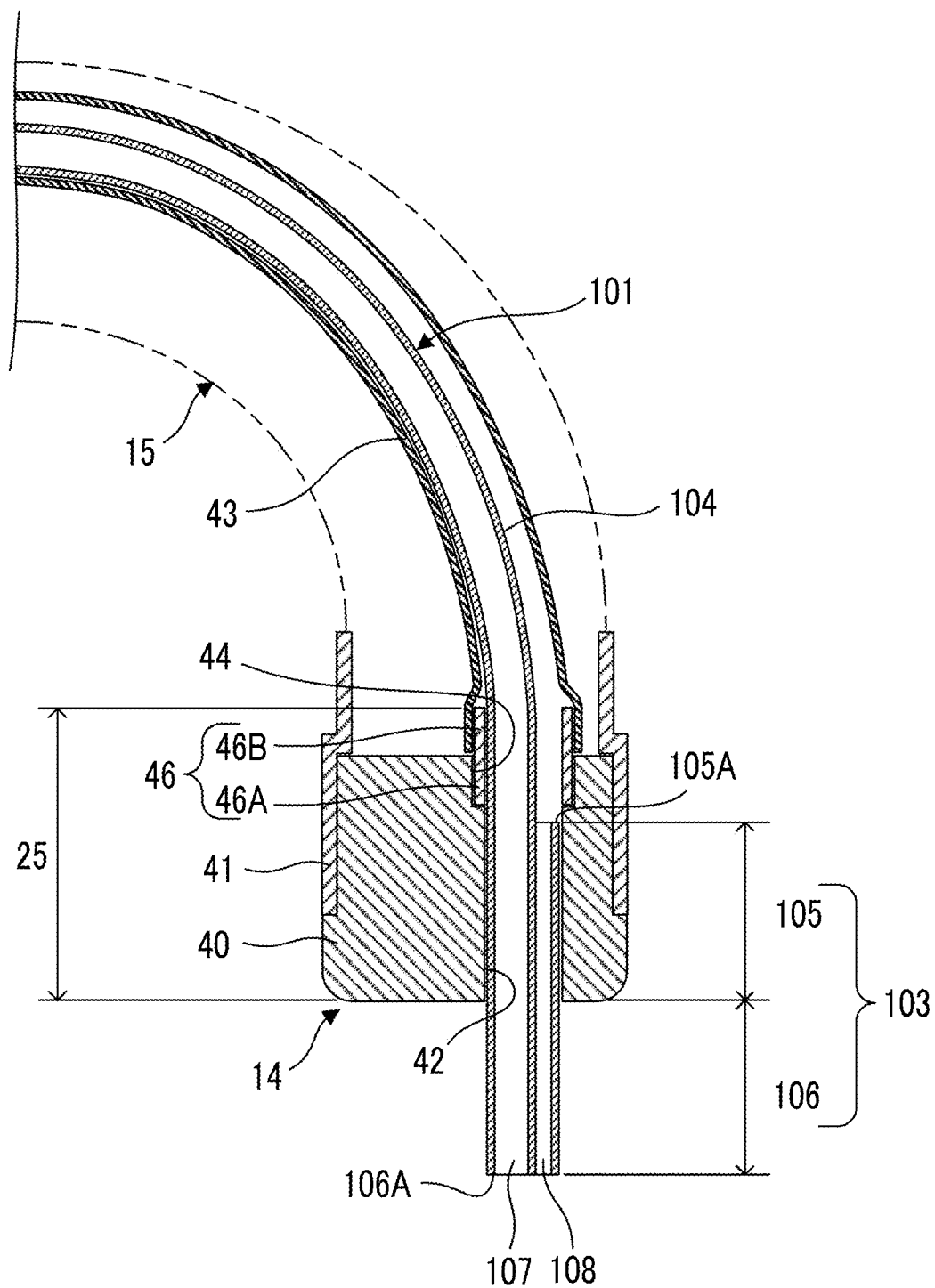
FIG. 7 is a cross-sectional view of another example of the outlet portion of the treatment tool insertion channel in the state where the endoscope aid of FIG. 4 is attached to the treatment tool insertion channel of the endoscope of FIG. 1.

In the example illustrated in FIG. 7, a fitting hole 44, which is coaxial with the through-hole 42 and has a larger diameter than the through-hole 42, is formed in the proximal end part of the distal end rigid part 40, and a distal end part 46A of a hard connection pipe 46 that is a member different from the distal end rigid part 40, is internally fitted the fitting hole 44. The distal end of the channel tube 43 is externally fitted to a proximal end part 46B of the connection pipe 46 protruding from the fitting hole 44. The through-hole 42, the fitting hole 44, and the connection pipe 46 are maintained in the shape of a straight pipe irrespective of the bending of the bending part 15. In this case, the outlet portion 25 of the treatment tool insertion channel 23 is constituted of the through-hole 42, the fitting hole 44, and the connection pipe 46.

Figure 8:
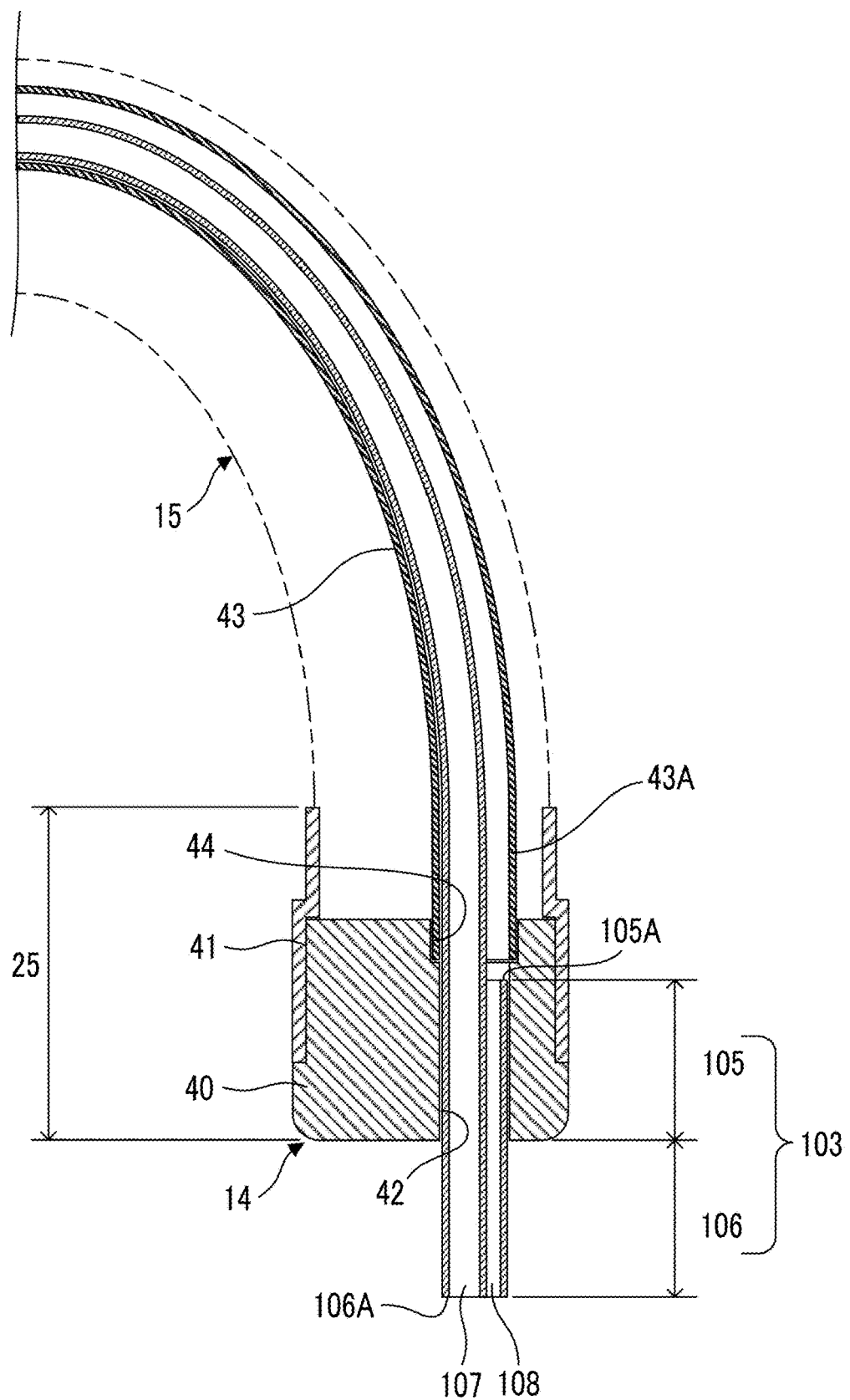
FIG. 8 is a cross-sectional view of a further example of the outlet portion of the treatment tool insertion channel in the state where the endoscope aid of FIG. 4 is attached to the treatment tool insertion channel of the endoscope of FIG. 1.

In the example illustrated in FIG. 8, the maximum rotational movement angle of a set of two adjacent pieces 50 disposed nearest to the distal end part 14 side among the plurality of pieces 50 (refer to FIG. 3) included in the bending part 15 is extremely small, and a distal end part 43A of the channel tube 43 disposed inside the distal end sleeve 41 of the distal end part 14 is maintained in the shape of a straight pipe irrespective of the bending of the bending part 15. The outlet portion 25 of the treatment tool insertion channel 23 is constituted of the through-hole 42, the fitting hole 44, and the distal end part 43A of the channel tube 43.

In addition, whether or not the channel tube 43 is straight can be estimated depending on the straightness of the channel tube 43 in the longitudinal axis, and in a case where the straightness of a portion to be evaluated in the longitudinal axis is 10% or less of the internal diameter of the channel tube 43, the portion to be evaluated is straight. Additionally, in a case where two or more sets of two pieces 50 of which the maximum rotational movement angle is extremely small are continuously provided from the distal end part 14 side, there is a case where the outlet portion 25 reaches the insides of one or a plurality of pieces 50 disposed on the distal end part 14 side.

The tubular member 101 is longer than the total length of the treatment tool insertion channel 23, and the distal end part 103 of the tubular member 101 has a sliding contact part 105 disposed in the outlet portion 25 of the treatment tool insertion channel 23, and an extending part 106 extending from the sliding contact part 105 to the distal end side. The sliding contact part 105 has an outer periphery coming in sliding contact with an inner peripheral surface of the outlet portion 25. In the tubular member 101 having a circular cross-sectional shape, an outer peripheral surface of the sliding contact part 105 comes in sliding contact with the inner peripheral surface of the outlet portion 25. In a case where the inner peripheral surface of the outlet portion 25 and the outer peripheral surface of the distal end part 103 come in sliding contact with each other, it is desirable that the internal diameter of the outlet portion 25 and the external diameter of the distal end part 103 has a so-called clearance fit relationship (External diameter of outlet portion 25>Internal diameter of distal end part 103). However, in a case where the material of the treatment tool insertion channel 23 is flexible, a tight fit relationship (External diameter of outlet portion 25<Internal diameter of distal end part 103) may be established. The extending part 106 is disposed to protrude from the opening (outlet) of the outlet portion 25 of the treatment tool insertion channel 23.

The tubular member 101 has the treatment tool insertion pipe line 107 through which a treatment tool is inserted, and a suction pipe line 108 to be used for suction of liquid, such as blood. The treatment tool insertion pipe line 107 extends from the proximal end part of the tubular member 101 to the distal end part 103, and a distal-end-side opening of the treatment tool insertion pipe line 107 is provided in a distal end surface 106A of the extending part 106. The suction pipe line 108 passes through the distal end part 103 in the axial direction, a proximal-end-side opening of the suction pipe line 108 is provided in a proximal end surface 105A of the sliding contact part 105, and a distal-end-side opening of the suction pipe line 108 is provided in the distal end surface 106A of the extending part 106.

As the inner peripheral surface of the outlet portion 25 of the treatment tool insertion channel 23 and the outer peripheral surface of the sliding contact part 105 of the tubular member 101 come in sliding contact with each other, the disposition of the distal end part 103 in the outlet portion 25 is stable. Accordingly, a central axis of an inner hole of the outlet portion 25 maintained in the shape of a straight pipe irrespective of the bending of the bending part 15, and a central axis of the treatment tool insertion pipe line 107 in the distal end part 103 are parallel to each other.

Figure 9:
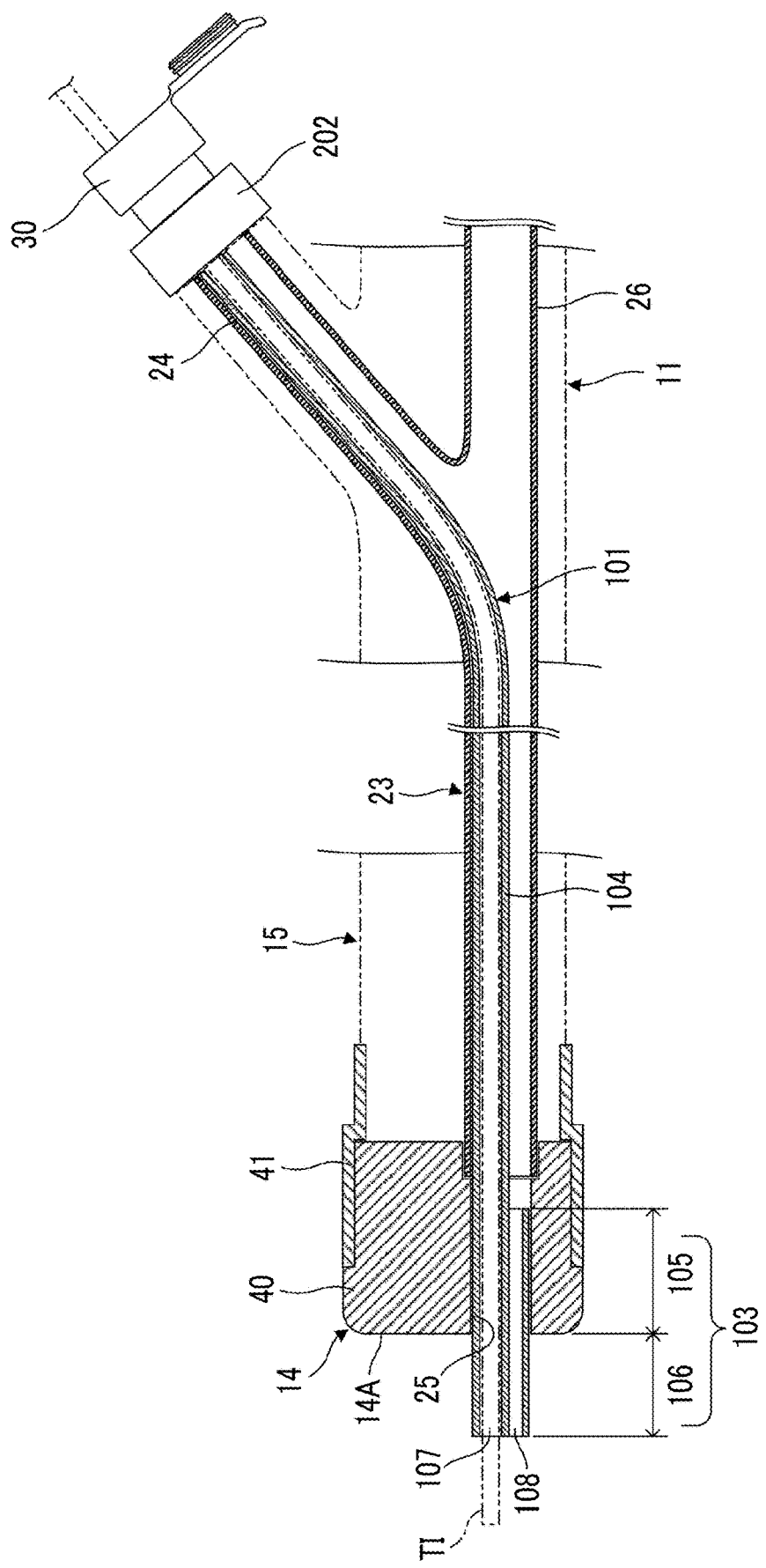
FIG. 9 is a schematic view illustrating an example of a method of using the endoscope aid of FIG. 4.

FIG. 9 illustrates an example of a method of using the endoscope aid 100.

The above endoscope aid 100 is used in combination with a treatment tool TI with a smaller size than the internal diameter of the treatment tool insertion channel 23. The treatment tool TI is, for example, a puncturing needle, high-frequency scissors forceps, a high-frequency knife, bipolar hemostatic forceps, a clip, a collection net, or the like.

First, the tubular member 101 of the endoscope aid 100 is inserted into the treatment tool insertion channel 23. The sliding contact part 105 of the distal end part 103 of the tubular member 101 is disposed in the outlet portion 25 of the treatment tool insertion channel 23, and the extending part 106 of the distal end part 103 is disposed to protrude from the opening of the outlet portion 25 of the treatment tool insertion channel 23. Next, the treatment tool TI is inserted into the treatment tool insertion pipe line 107 of the tubular member 101 through the opening of the mouthpiece 102 of the endoscope aid 100.

The treatment tool TI inserted into the treatment tool insertion pipe line 107 of the tubular member 101 is guided to the distal end part 103 of the tubular member 101 by the treatment tool insertion pipe line 107, and protrudes from the distal-end-side opening of the treatment tool insertion pipe line 107. The treatment tool TI protrudes onto the central axis of the treatment tool insertion pipe line 107 in the distal end part 103. Since the central axis of the treatment tool insertion pipe line 107 and the central axis of the inner hole of the outlet portion 25 are parallel to each other, the treatment tool TI protrudes along the central axis of the inner hole of the outlet portion 25. Accordingly, the disposition of the treatment tool TI is stable.

As the outer peripheral surface of the sliding contact part 105 of the tubular member 101 comes in sliding contact with the inner peripheral surface of the outlet portion 25 of the treatment tool insertion channel 23, the disposition of the distal end part 103 of the tubular member 101 in the outlet portion 25 is stable. On the other hand, the opening of the outlet portion 25 leading to the suction tube 26 is substantially air-tightly blocked by the distal end part 103. However, the suction pipe line 108 passing through the distal end part 103 in the axial direction is connected to the suction tube 26 via a gap formed between the inner peripheral surface of the treatment tool insertion channel 23 and the outer peripheral surface of the smaller-diameter part 104 of the tubular member 101, and the suction tube 26 and the outside is caused to communicate with each other. Accordingly, even in a state where the tubular member 101 is inserted into the treatment tool insertion channel 23, it is possible to perform suction through the suction pipe line 108.

The distal-end-side opening of the suction pipe line 108 serving as a suction port is provided in the extending part 106 of the tubular member 101 in a state where the tubular member 101 is inserted into the treatment tool insertion channel 23, and the extending part 106 is disposed to protrude from the opening of the outlet portion 25 of the treatment tool insertion channel 23. Accordingly, for example, in a case where the distal-end-side opening of the suction pipe line 108 is disposed in the vicinity of the treatment target part that is bleeding and blood is suctioned, the distance between the distal end surface 14A of the distal end part 14 of the insertion part 10 provided with the observation window of the imaging unit 17 (refer to FIG. 2), and the treatment target part is maintained, and it is possible to secure a visual field. The length of the extending part 106 disposed to protrude from the opening of the outlet portion 25 is preferably about 20 mm in a case where the securement of the visual field is taken into consideration.

Figure 10:
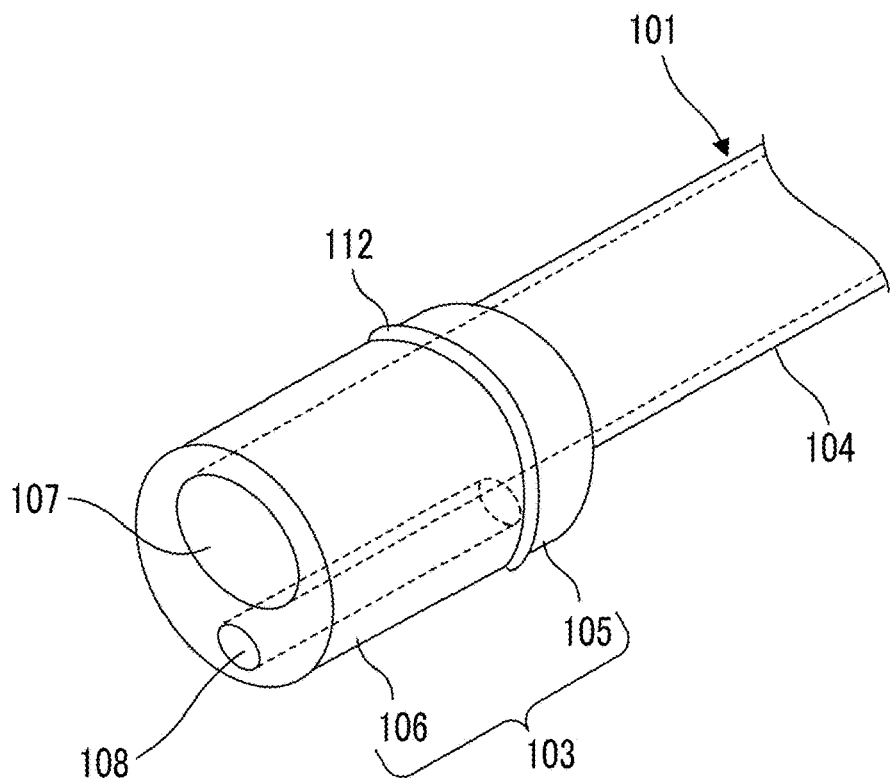
FIG. 10 is a perspective view of a modification example of the endoscope aid of FIG. 4.
Figure 11:
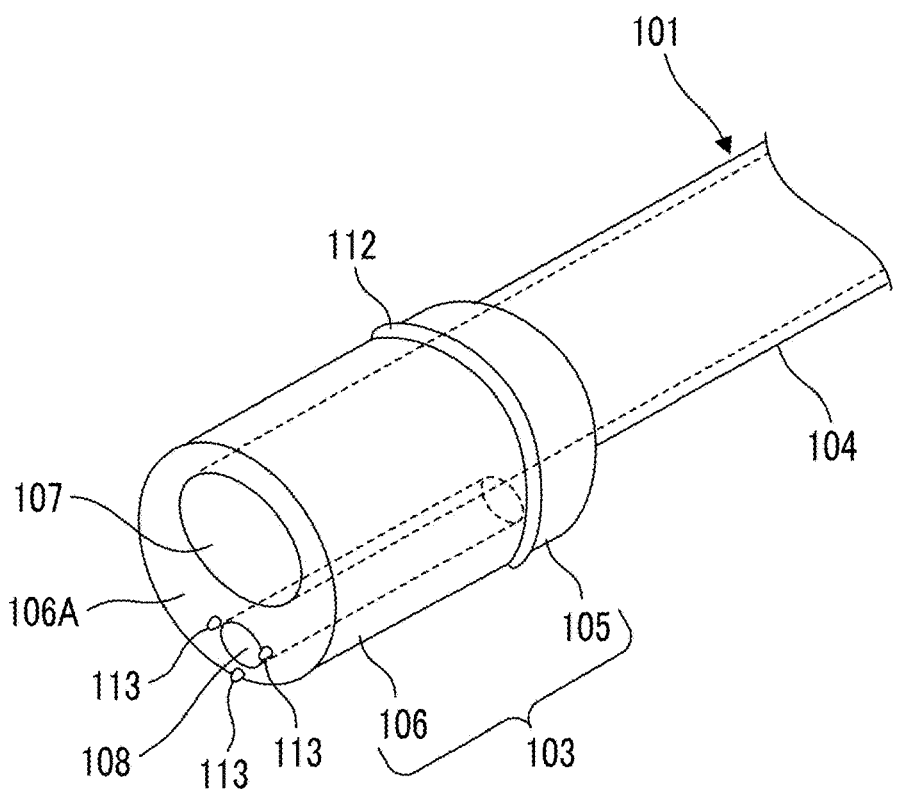
FIG. 11 is a perspective view of another modification example of the endoscope aid of FIG. 4.

FIGS. 10 and 11 illustrate modification examples of the endoscope aid 100, respectively.

In the example illustrated in FIG. 10, the tubular projection 112 is provided on the outer peripheral surface of the sliding contact part 105 of the tubular member 101, and the tubular projection 112 comes in sliding contact with the inner peripheral surface of the outlet portion 25 of the treatment tool insertion channel 23. As the tubular projection 112 is in sliding contact with the inner peripheral surface of the outlet portion 25, the area of contact is smaller than that in a case where the entire outer peripheral surface of the sliding contact part 105 is in sliding contact with the inner peripheral surface of the outlet portion 25. Accordingly, the frictional resistance in a case where the tubular member 101 is pushed into the treatment tool insertion channel 23 and is pulled from the treatment tool insertion channel 23, can be reduced, and handling of the endoscope aid 100 can be made easy.

The tubular projection 112 may be formed integrally with the tubular member 101, or may be formed of a seal member, such as an O-ring separate from the tubular member 101. Additionally, the tubular projection 112 is not limited to one, and a plurality of the tubular projections 112 may be provided at intervals in the axial direction in consideration of the stability of the distal end part 103 of the tubular member 101 in the outlet portion 25 of the treatment tool insertion channel 23, and the balance with the frictional resistance.

In the example illustrated in FIG. 11, projections 113 are provided around the distal-end-side opening of the suction pipe line 108. The distal-end-side opening of the suction pipe line 108 is provided in the distal end surface 106A of the extending part 106 of the tubular member 101, and is directed to the axial direction of the distal end part of the tubular member 101. For example, in a case where the distal-end-side opening of the suction pipe line 108 is disposed in the vicinity of the treatment target part that is bleeding and blood is suctioned, there is a case where the treatment target part sticks to the distal-end-side opening of the suction pipe line 108. However, as the projections 113 are provided around the distal-end-side opening of the suction pipe line 108, the sticking of the treatment target part is suppressed. This allows stable suction through the suction pipe line 108. The number of projections 113 is not particularly limited, may be one or plural.

Figure 12:
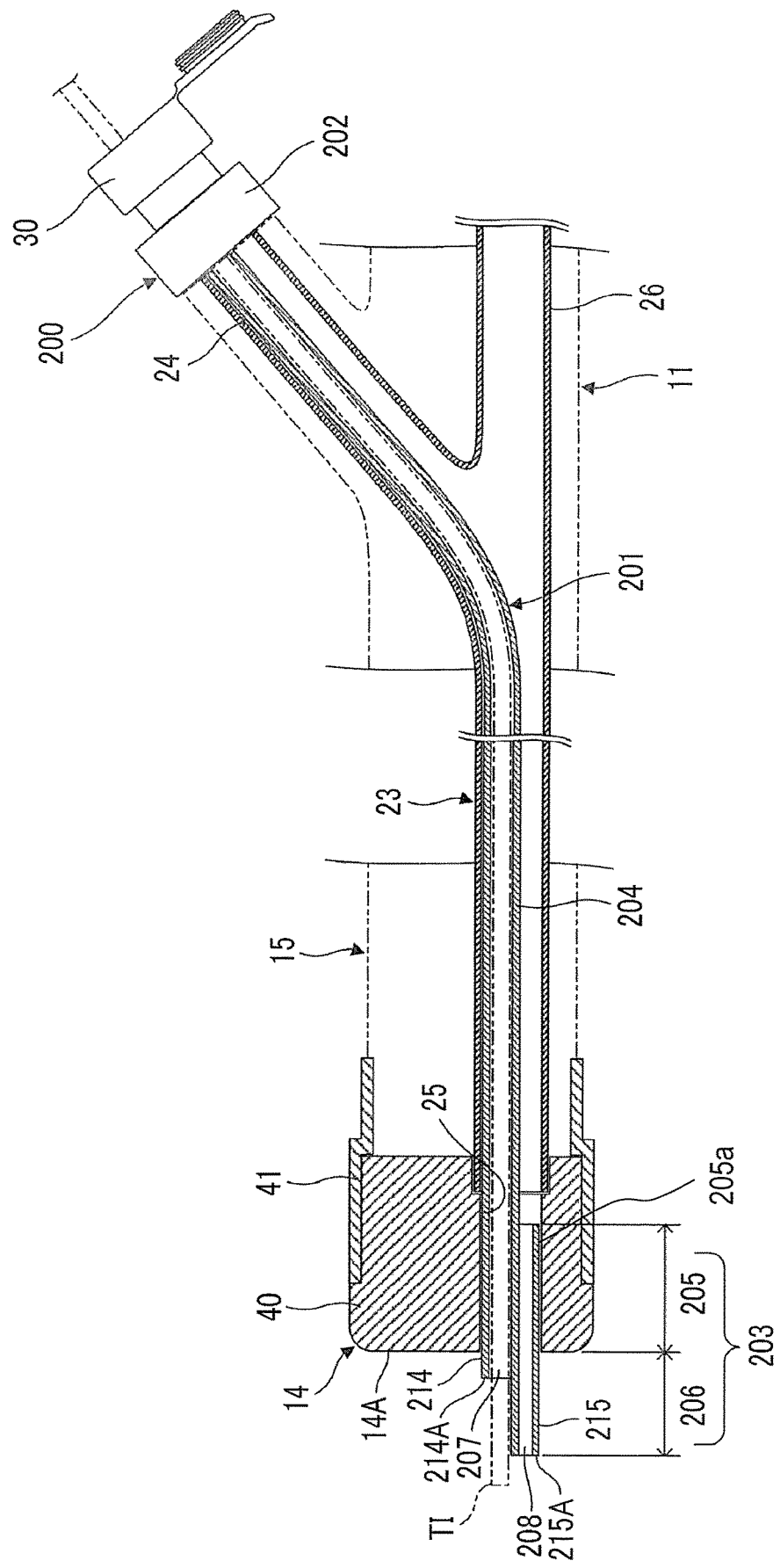
FIG. 12 is a cross-sectional view of another example of the endoscope aid for describing the embodiment of the invention.

FIG. 12 illustrates another example of the endoscope aid for describing the embodiment of the invention.

An endoscope aid 200 illustrated in FIG. 12 is attachably and detachably attached to the treatment tool insertion channel 23 of the endoscope 2. The endoscope aid 200 has a flexible tubular member 201 having a circular cross-sectional shape, and a mouthpiece 202 coupled to a proximal end part of the tubular member 201. The tubular member 201 is longer than the total length of the treatment tool insertion channel 23, and a distal end part 203 of the tubular member 201 has a sliding contact part 205 disposed in the outlet portion 25 of the treatment tool insertion channel 23, and an extending part 206 disposed to protrude from the opening of the outlet portion 25. An outer peripheral surface of the sliding contact part 205 comes in sliding contact with the inner peripheral surface of the outlet portion 25. Additionally, the other portion excluding the distal end part 203 of the tubular member 201 is a smaller-diameter part 204 thinner than the distal end part 203.

The tubular member 201 has a treatment tool insertion pipe line 207 and a suction pipe line 208. The proximal-end-side opening of the suction pipe line 208 is provided in the proximal end surface 205A of the sliding contact part 205, and the distal-end-side opening of the suction pipe line 208 is provided in the distal end surface of the extending part 206. The suction pipe line 208 passing through the distal end part 203 (the sliding contact part 205 and the extending part 206) in the axial direction is connected to the suction tube 26 via a gap formed between the inner peripheral surface of the treatment tool insertion channel 23 and the outer peripheral surface of the smaller-diameter part 204 of the tubular member 201, and causes the suction tube 26 and the outside to communicate with each other.

The treatment tool insertion pipe line 207 extends from a proximal end part of the tubular member 201 to which the mouthpiece 202 is coupled to the distal end part 203, and a distal-end-side opening of the treatment tool insertion pipe line 207 is provided in the extending part 206 and is provided nearer to the proximal end side than the distal-end-side opening of the suction pipe line 208. Specifically, the extending part 206 is formed in a step-like shape having a first portion 214, and a second portion 215 extending farther toward the distal end side than the first portion 214, the distal-end-side opening of the treatment tool insertion pipe line 207 is provided in a distal end surface 214A of the first portion 214, and the distal-end-side opening of the suction pipe line 208 is provided in a distal end surface 215A of the second portion 215.

According to the endoscope aid 200, for example, in a case where the distal-end-side opening of the suction pipe line 208 is disposed in the vicinity of the treatment target part that is bleeding and blood is suctioned, the distance between the distal end surface 14A of the distal end part 14 of the insertion part 10 provided with the observation window of the imaging unit 17 (refer to FIG. 2), and the treatment target part is maintained, and it is possible to secure the visual field. Also, the distance between the distal end surface 214A of the first portion 214 of the extending part 206 provided with the distal-end-side opening of the treatment tool insertion pipe line 207, and treatment target part can also be maintained. Accordingly, a surgical field required for treatment can be secured, and treatment, such as hemostasis, can be performed simultaneously with the suction.

In addition, similarly to the example illustrated in FIG. 10, one or more tubular projections may be provided on the outer peripheral surface of the sliding contact part 205 of the tubular member 201 from a viewpoint of reducing the frictional resistance between the tubular member 201 and the treatment tool insertion channel 23. Additionally, similarly to the example additionally illustrated in FIG. 11, one or more projections may be provided around the distal-end-side opening of the suction pipe line 208 from a viewpoint of suppressing the sticking of the treatment target part to the distal-end-side opening of the suction pipe line 208.

Figure 13:
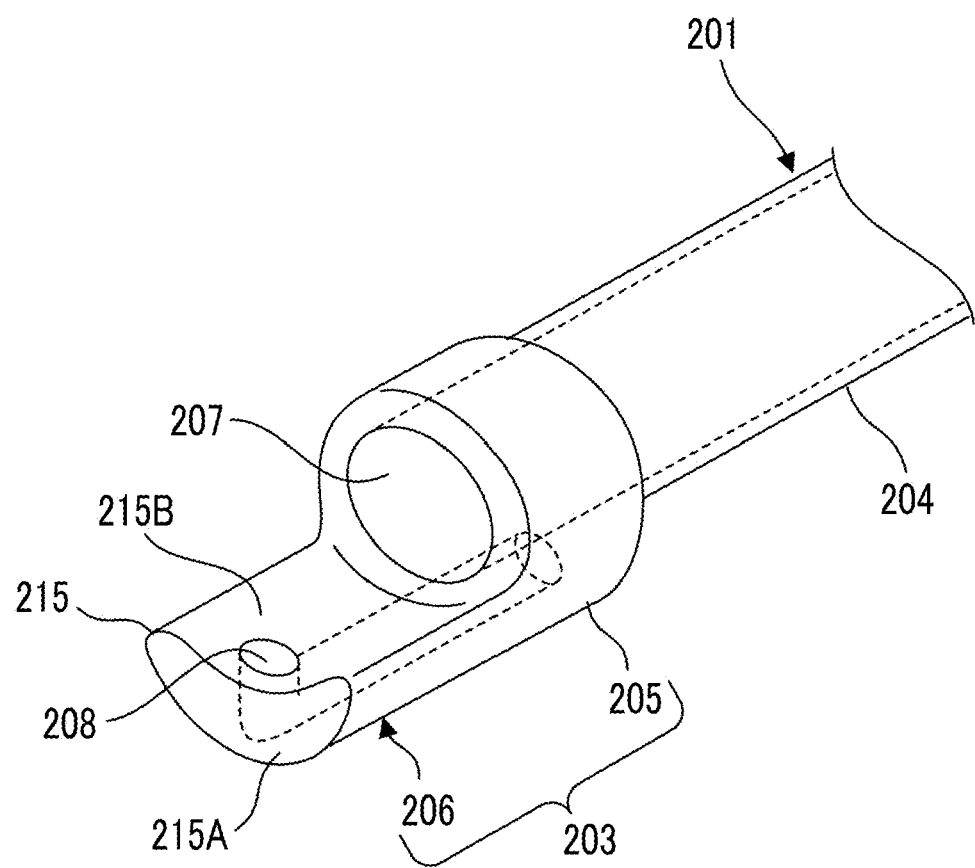
FIG. 13 is a perspective view of the modification example of the endoscope aid of FIG. 12.

FIG. 13 illustrates a modification example of the endoscope aid 200.

In the example illustrated in FIG. 13, a distal-end-side opening of the suction pipe line 208 is provided in an outer peripheral surface of the second portion 215 instead of the distal end surface 215A of the second portion 215 of the extending part 206. The distal-end-side opening of the suction pipe line 208 provided in the outer peripheral surface of the second portion 215 is directed to a direction that intersects the axial direction of the distal end part 203 of the tubular member 201. Accordingly, the sticking of the treatment target part is suppressed, and stable suction through the suction pipe line 108 is allowed.

In a case where the distal-end-side opening of the suction pipe line 208 is provided in the outer peripheral surface of the second portion 215, preferably, the distal-end-side opening of the suction pipe line 208 is provided in the upper surface 215B of the second portion 215, which faces a treatment tool protruding from the distal-end-side opening of the treatment tool insertion pipe line 207, in an outer peripheral surface of the second portion 215. Accordingly, the blood accumulated in the surgical field where treatment is performed can be effectively suctioned.

The cases where the suction pipe line 108 of the endoscope aid 100 is provided only in the distal end part 103 of the tubular member 101, the suction pipe line 208 of the endoscope aid 200 is also provided only in the distal end part 203 of the tubular member 201, and both the suction pipe line 108 and the suction pipe line 208 are connected to the suction tube 26 of the endoscope 2 have been described hitherto. However, a suction pipe line may be provided to extend from a proximal end part of a tubular member to a distal end part thereof in parallel with a treatment tool insertion pipe line.

Figure 14:
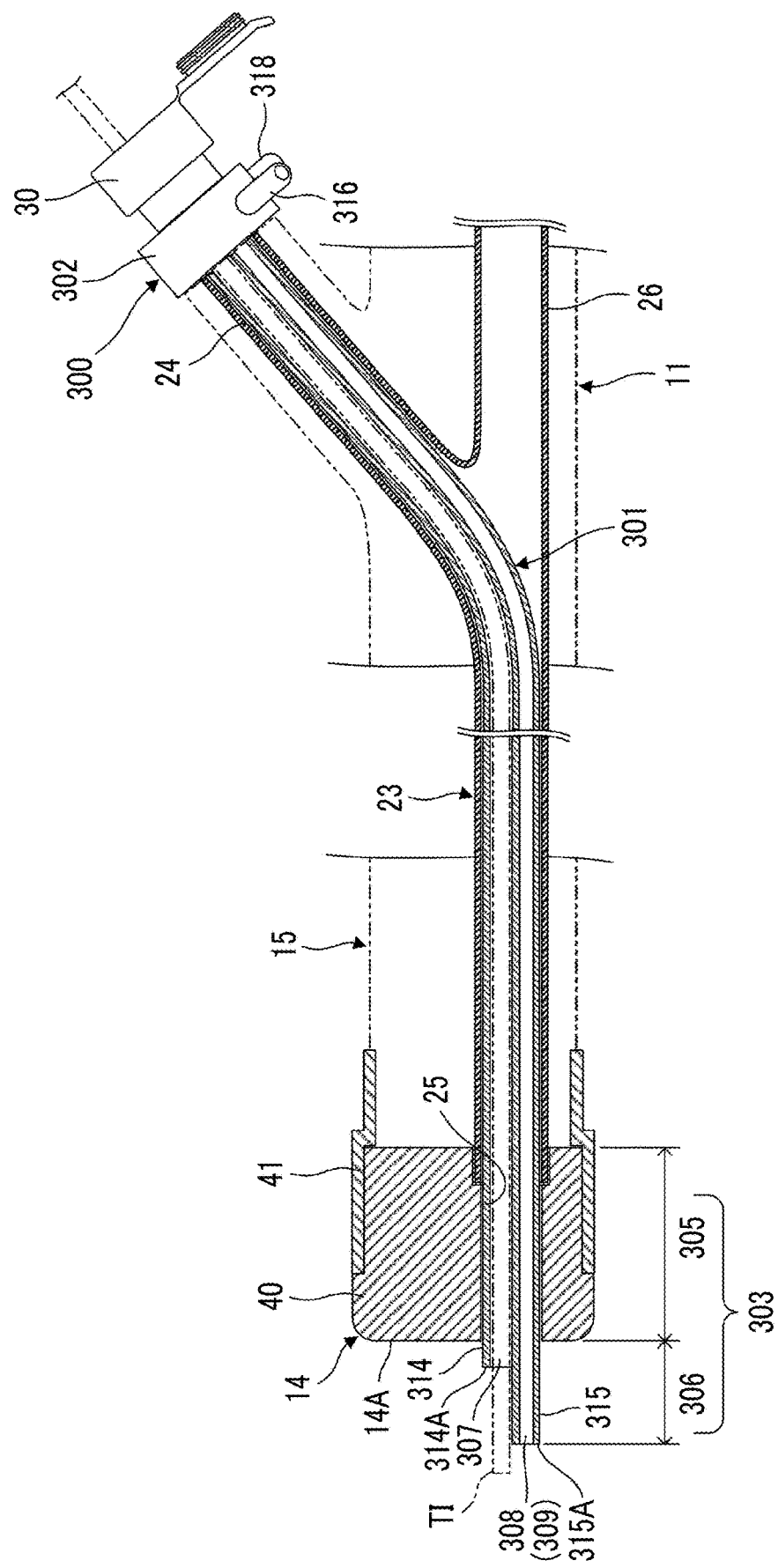
FIG. 14 is a cross-sectional view of a further example of the endoscope aid for describing the embodiment of the invention.
Figure 15:
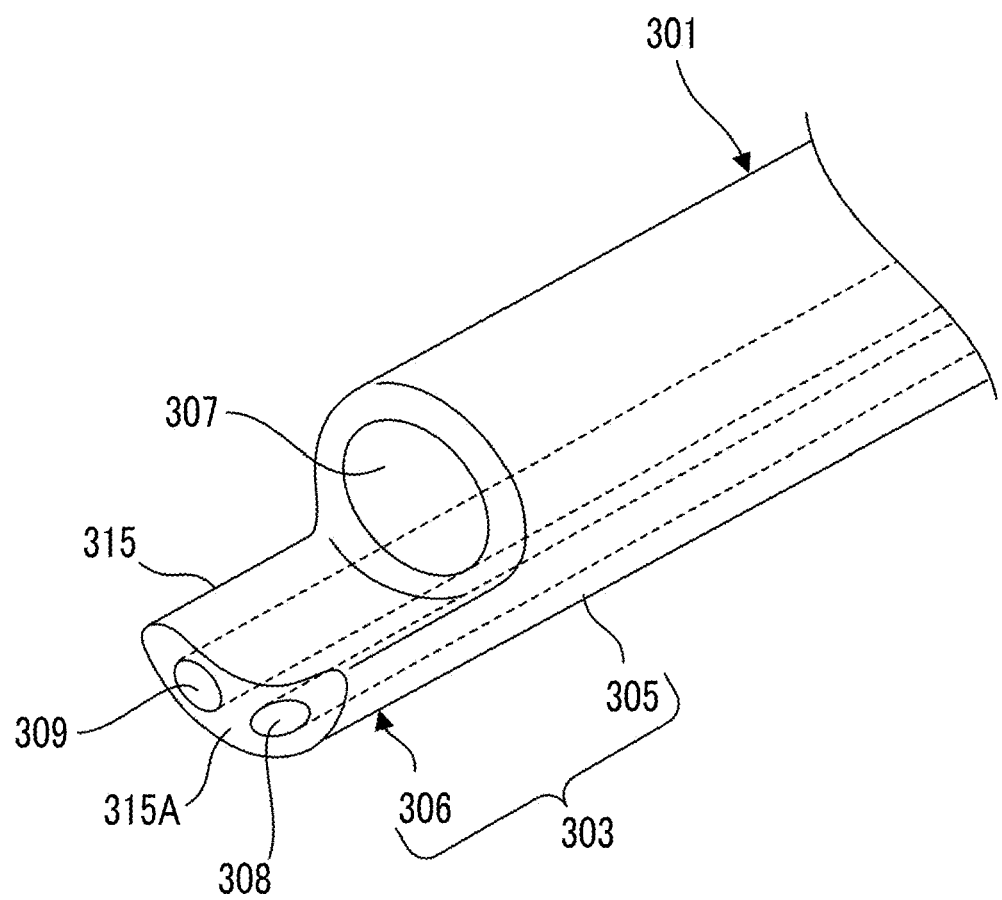
FIG. 15 is a perspective view of the endoscope aid of FIG. 14.

FIGS. 14 and 15 illustrate further examples of the endoscope aids for describing the embodiment of the invention.

An endoscope aid 300 illustrated in FIG. 14 is attachably and detachably attached to the treatment tool insertion channel 23 of the endoscope 2. The endoscope aid 300 has a flexible tubular member 301 having a circular cross-sectional shape, and a mouthpiece 302 coupled to a proximal end part of the tubular member 301. The tubular member 301 is longer than the total length of the treatment tool insertion channel 23, and a distal end part 303 of the tubular member 301 has a sliding contact part 305 disposed in the outlet portion 25 of the treatment tool insertion channel 23, and an extending part 306 disposed to protrude from the opening of the outlet portion 25.

The tubular member 301 has a treatment tool insertion pipe line 307 and a suction pipe line 308. The treatment tool insertion pipe line 307 extends from a proximal end part of the tubular member 301 to which the mouthpiece 202 is coupled to the distal end part 303, and a distal-end-side opening of the treatment tool insertion pipe line 307 is provided in a distal end surface 314A of a first portion 314 of the extending part 306. The suction pipe line 308 also extends from a proximal end part of the tubular member 301 to the distal end part 303, and a distal-end-side opening of the suction pipe line 308 is provided in a distal end surface 315A of a second portion 315 of the extending part 306. The mouthpiece 302 is provided with an opening (not illustrated) leading to the proximal-end-side opening of the treatment tool insertion pipe line 307, and a connecting part 316 leading to the proximal-end-side opening of the suction pipe line 308. The suction pipe line 308 is connected to a suction pump (not illustrated) via a connection tube (not illustrated) to be connected to the connecting part 316.

The tubular member 301 further has a liquid supply pipe line 309 that circulates liquid, such as a cleaning liquid. The liquid supply pipe line 309 extends from the proximal end part of the tubular member 301 to the distal end part 303, and a distal-end-side opening of the liquid supply pipe line 309 is provided in the distal end surface 315A of the second portion 315 of the extending part 306. The mouthpiece 302 is further provided with a connecting part 318 leading to a proximal-end-side opening of the liquid supply pipe line 309, and the liquid supply pipe line 309 is connected to a liquid supply pump (not illustrated) via a connection tube (not illustrated) to be connected to the connecting part 318.

For example, as one in which the cleaning liquid is supplied to the liquid supply pipe line 309 from a liquid supply pump, the cleaning liquid is jetted from the distal-end-side opening of the liquid supply pipe line 309. Accordingly, the treatment target part that is bleeding can be cleaned, and treatment becomes easy. In addition, the liquid supply pipe line 309 is also applicable to the tubular member 101 of the endoscope aid 100 and the tubular member 201 of the endoscope aid 200 as described above.

As described above, an endoscope aid disclosed in the present specification is an endoscope aid attachably and detachably attached to a treatment tool insertion channel of an endoscope. The endoscope aid comprises a flexible tubular member longer than a total length of the treatment tool insertion channel. The tubular member has a treatment tool insertion pipe line that extends from a proximal end part of the tubular member disposed on an inlet side of the treatment tool insertion channel to a distal end part of the tubular member, and a suction pipe line that is provided separately from the treatment tool insertion pipe line. The distal end part of the tubular member has a sliding contact part that has an outer periphery coming in sliding contact with an inner peripheral surface of an outlet portion of the treatment tool insertion channel maintained in the shape of a straight pipe irrespective of bending of an endoscope bending part and is disposed in the outlet portion, and an extending part that extends from the sliding contact part to a distal end side and is disposed to protrude from an outlet of the treatment tool insertion channel. A distal-end-side opening of the suction pipe line is provided in the extending part.

Additionally, in the endoscope aid disclosed in the present specification, a suction tube of the endoscope joins the treatment tool insertion channel, the other portion excluding the distal end part of the tubular member is a smaller-diameter part thinner than the distal end part, and a proximal-end-side opening of the suction pipe line is connected to a gap formed between an inner peripheral surface of the treatment tool insertion channel and an outer peripheral surface of the smaller-diameter part.

Additionally, in the endoscope aid disclosed in the present specification, the outer periphery of the sliding contact part is formed by one or more annular projections provided on an outer peripheral surface of the sliding contact part.

Additionally, in the endoscope aid disclosed in the present specification, a distal-end-side opening of the treatment tool insertion pipe line is provided in the extending part, and is provided nearer to a proximal end side than the distal-end-side opening of the suction pipe line.

Additionally, in the endoscope aid disclosed in the present specification, the distal-end-side opening of the suction pipe line is directed to a direction that intersects an axial direction of the distal end part of the tubular member.

Additionally, in the endoscope aid disclosed in the present specification, the distal-end-side opening of the suction pipe line is directed to an axial direction of the distal end part of the tubular member, and one or more projections are provided around the distal-end-side opening of the suction pipe line.

Additionally, in the endoscope aid disclosed in the present specification, the tubular member has a liquid supply pipe line that extends from the proximal end part of the tubular member disposed on the inlet side of the treatment tool insertion channel to the distal end part of the tubular member.

Additionally, an endoscope disclosed in the present specification comprises a treatment tool insertion channel to which the above endoscope aid is attachable.

EXPLANATION OF REFERENCES

1: endoscope system
2: endoscope
3: light source device
4: processor unit
5: suction pump
6: monitor
10: insertion part
11: operating part
12: universal cord
13: connector
14: distal end part
14A: distal end surface of distal end part
15: bending part
16: flexible part
17: imaging unit
18A: operation button
18B: operation knob
18C: operation button
20: light guide
21: electrical cable
22, 22A, 22B: operating wire
23: treatment tool insertion channel
24: inlet portion of treatment tool insertion channel
25: outlet portion of treatment tool insertion channel
26: suction tube
27: valve
28: mouthpiece
29: connection tube
30: forceps valve
40: distal end rigid part
41: distal end sleeve
42: through-hole
43: channel tube
43A: distal end part of channel tube
44: fitting hole
45: annular protrusion
46: connection pipe
46A: distal end part of connection pipe
46B: proximal end part of connection pipe
50: piece
51: shaft member
100: endoscope aid
101: tubular member
102: mouthpiece
103: distal end part of tubular member
104: smaller-diameter part
105: sliding contact part
105A: proximal end surface of sliding contact part
106: extending part
106A: distal end surface of extending part
107: tubular projection
107: treatment tool insertion pipe line
108: suction pipe line
112: tubular projection
113: projection
200: endoscope aid
201: tubular member
202: mouthpiece
203: distal end part of tubular member
204: smaller-diameter part
205: sliding contact part
205A: proximal end surface of sliding contact part
206: extending part
207: treatment tool insertion pipe line
208: suction pipe line
214: first portion of extending part
214A: distal end surface of first portion of extending part
215: second portion of extending part
215A: distal end surface of second portion of extending part
215B: upper surface of second portion of extending part
300: endoscope aid
301: tubular member
302: mouthpiece
303: distal end part of tubular member
305: sliding contact part
306: extending part
307: treatment tool insertion pipe line
308: suction pipe line
309: liquid supply pipe line
314: first portion of extending part
314A: distal end surface of first portion of extending part
315: second portion of extending part
315A: distal end surface of second portion of extending part
316: connecting part
318: connecting part
Gx: spacing
Gy: spacing
TI: treatment tool
X: rotational movement axis
Y: rotational movement axis

What is claimed is:

1. An endoscope aid attachably and detachably attached to a treatment tool insertion channel of an endoscope, the endoscope aid comprising:
   a flexible tubular member longer than a total length of the treatment tool insertion channel,
   wherein the tubular member has
      a treatment tool insertion pipe line that extends from a proximal end part of the tubular member disposed on an inlet side of the treatment tool insertion channel to a distal end part of the tubular member, and
      a suction pipe line that is provided separately from the treatment tool insertion pipe line,
   wherein the distal end part of the tubular member has
      a sliding contact part that has an outer periphery coming in sliding contact with an inner peripheral surface of an outlet portion of the treatment tool insertion channel maintained in the shape of a straight pipe irrespective of bending of an endoscope bending part and is disposed in the outlet portion, and
      an extending part that extends from the sliding contact part to a distal end side and is disposed to protrude from an outlet of the treatment tool insertion channel, and
   wherein a distal-end-side opening of the suction pipe line is provided in the extending part,
      wherein a suction tube of the endoscope joins the treatment tool insertion channel,
      wherein the flexible tubular member includes a smaller-diameter part thinner than the distal end part, and
      wherein a proximal-end-side opening of the suction pipe line disposed at a proximal end of the suction pipe line opens into a gap formed between an inner peripheral surface of the treatment tool insertion channel and an outer peripheral surface of the smaller-diameter part.

2. The endoscope aid according to claim 1, wherein the outer periphery of the sliding contact part is formed by one or more annular projections provided on an outer peripheral surface of the sliding contact part.

3. The endoscope aid according to claim 2,
wherein a distal-end-side opening of the treatment tool insertion pipe line is provided in the extending part, and is provided nearer to a proximal end side than the distal-end-side opening of the suction pipe line.

4. The endoscope aid according to claim 3,
wherein the distal-end-side opening of the suction pipe line is directed to a direction that intersects an axial direction of the distal end part of the tubular member.

5. The endoscope aid according to claim 3,
wherein the distal-end-side opening of the suction pipe line is directed to an axial direction of the distal end part of the tubular member, and
wherein one or more projections are provided around the distal-end-side opening of the suction pipe line.

6. The endoscope aid according to claim 2,
wherein the distal-end-side opening of the suction pipe line is directed to a direction that intersects an axial direction of the distal end part of the tubular member.

7. The endoscope aid according to claim 2,
wherein the distal-end-side opening of the suction pipe line is directed to an axial direction of the distal end part of the tubular member, and
wherein one or more projections are provided around the distal-end-side opening of the suction pipe line.

8. The endoscope aid according to claim 1,
wherein a distal-end-side opening of the treatment tool insertion pipe line is provided in the extending part, and is provided nearer to a proximal end side than the distal-end-side opening of the suction pipe line.

9. The endoscope aid according to claim 8,
wherein the distal-end-side opening of the suction pipe line is directed to a direction that intersects an axial direction of the distal end part of the tubular member.

10. The endoscope aid according to claim 8,
wherein the distal-end-side opening of the suction pipe line is directed to an axial direction of the distal end part of the tubular member, and
wherein one or more projections are provided around the distal-end-side opening of the suction pipe line.

11. The endoscope aid according to claim 1,
wherein the distal-end-side opening of the suction pipe line is directed to a direction that intersects an axial direction of the distal end part of the tubular member.

12. The endoscope aid according to claim 1,
wherein the distal-end-side opening of the suction pipe line is directed to an axial direction of the distal end part of the tubular member, and
wherein one or more projections are provided around the distal-end-side opening of the suction pipe line.

13. The endoscope aid according to claim 1,
wherein the tubular member has a liquid supply pipe line that extends from the proximal end part of the tubular member disposed on the inlet side of the treatment tool insertion channel to the distal end part of the tubular member.

14. An endoscope comprising a treatment tool insertion channel to which the endoscope aid according to claim 1 is attachable.

* * * * *